United States Patent [19]

Cooperstein et al.

[11] 4,289,969
[45] Sep. 15, 1981

[54] RADIATION IMAGING APPARATUS

[75] Inventors: Gerald Cooperstein, Rockville, Md.; Richard C. Lanza; A. Robert Sohval, both of Cambridge, Mass.

[73] Assignee: Butler Greenwich Inc., Greenwich, Conn.

[21] Appl. No.: 922,982

[22] Filed: Jul. 10, 1978

[51] Int. Cl.³ ............................................. G03B 41/16
[52] U.S. Cl. ................................. 250/445 T; 250/402
[58] Field of Search .................. 250/445 T, 401, 402; 313/55

[56] References Cited
U.S. PATENT DOCUMENTS
4,129,783 12/1978 Houston .......................... 250/445 T Primary Examiner—Craig E. Church
Attorney, Agent, or Firm—Cesari and McKenna

[57] ABSTRACT

Radiation imaging apparatus especially suited for use in a computerized tomographic (CT) scanner employs an array of discrete X-ray sources, each being a cold cathode diode and an adjacent fixed array of closely packed radiation detectors to produce images of rapidly moving body organs such as the beating heart. A variety of alternative X-ray source embodiments are also disclosed.

19 Claims, 11 Drawing Figures

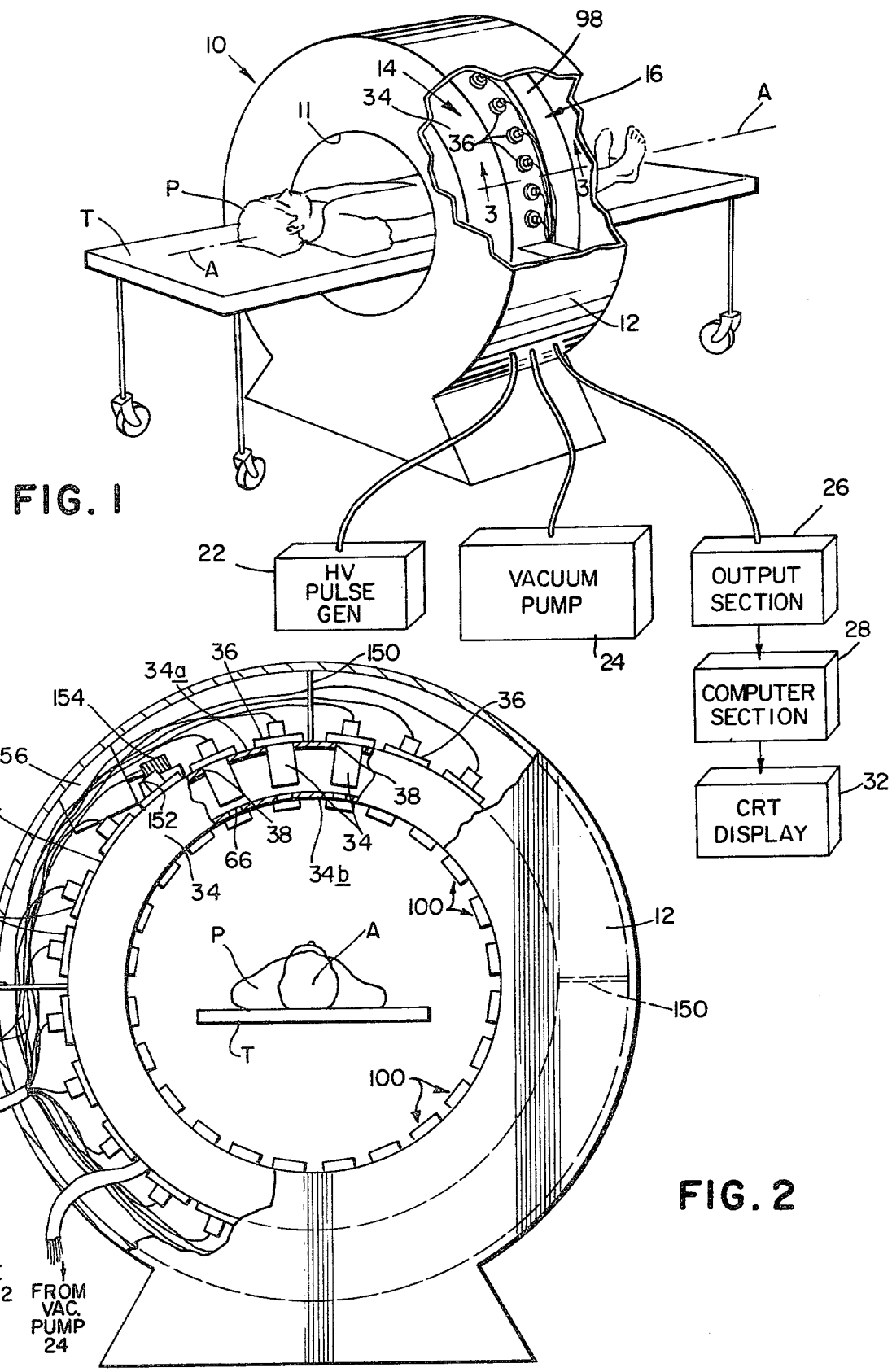

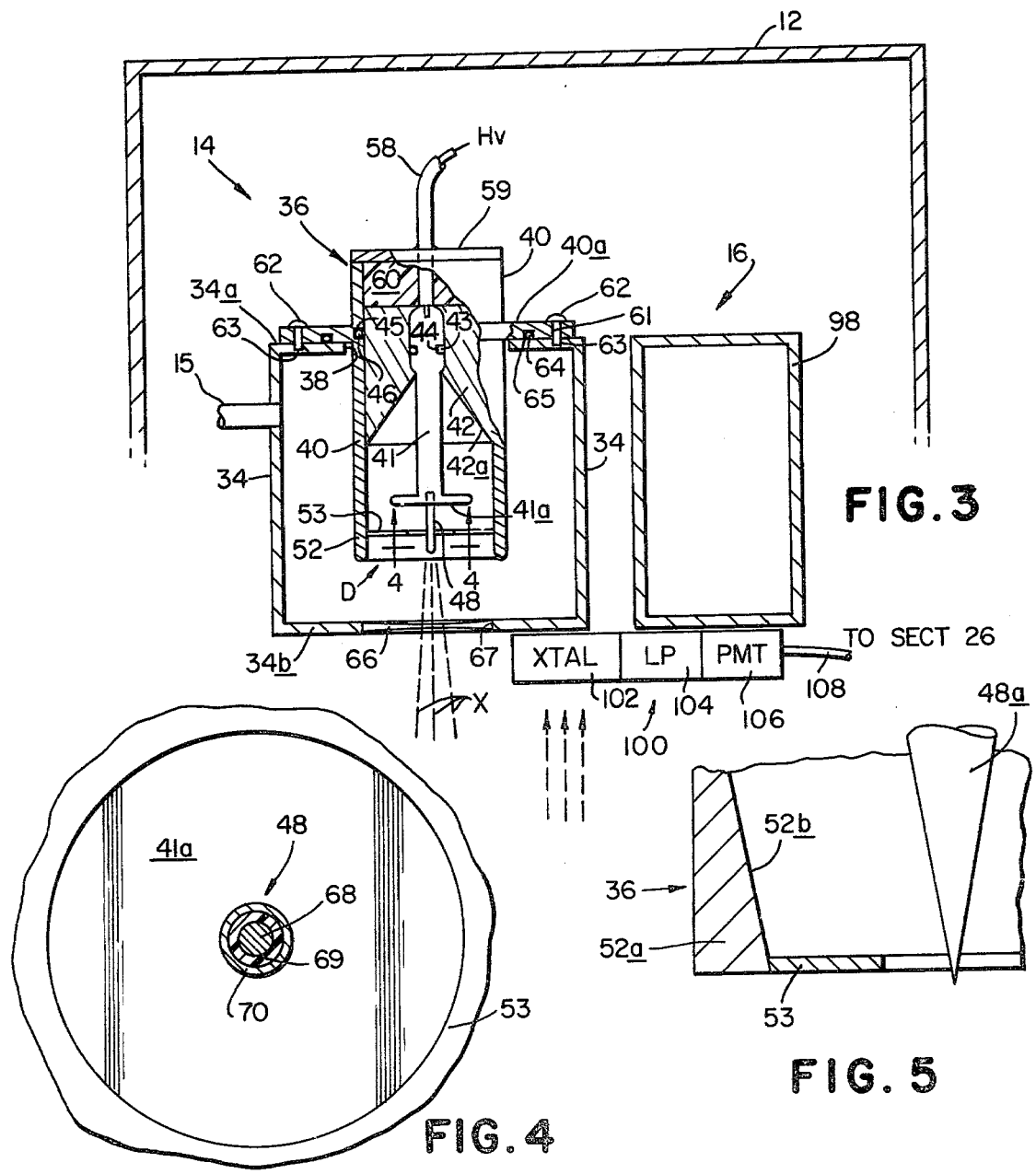
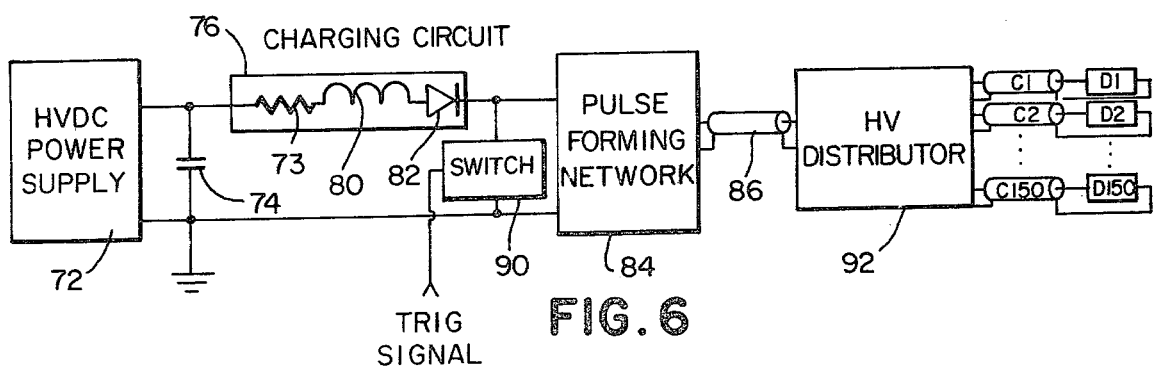

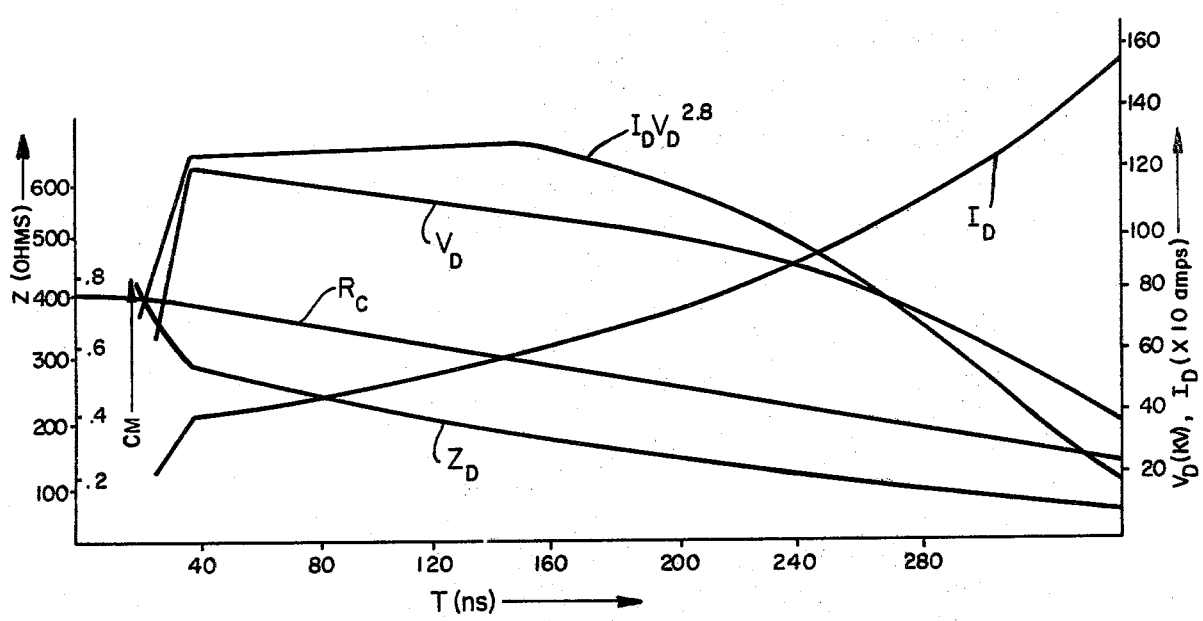
FIG. 9
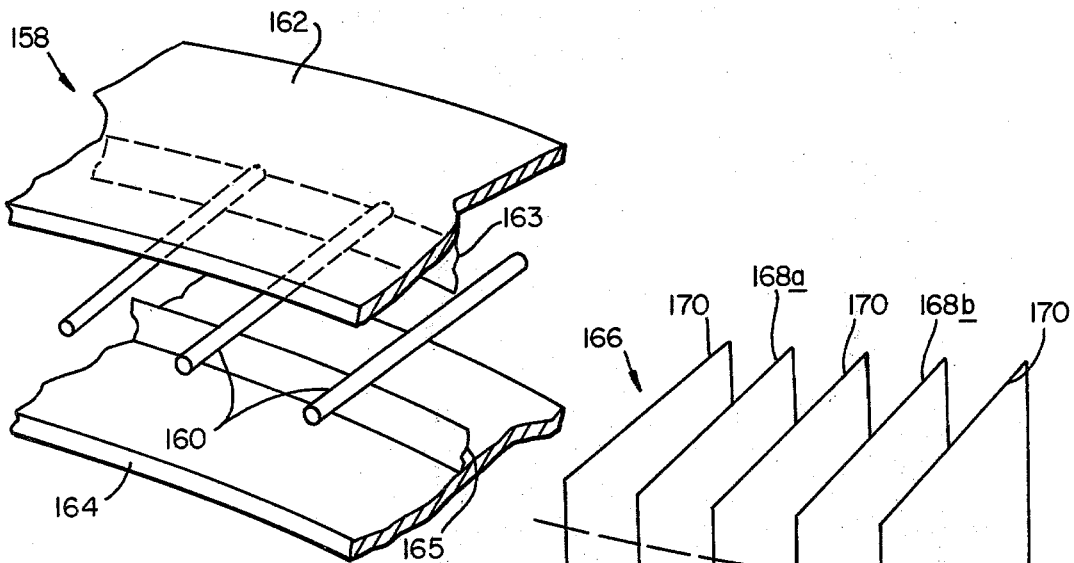
FIG. 10
FIG. 11

RADIATION IMAGING APPARATUS

This invention relates to a radiation imaging apparatus. It relates more particularly to apparatus of this general type which employs stationary X-ray source and detector arrays capable of acquiring multiple ultrafast scans per second to facilitate the dynamic study of moving human organs such as the beating heart. While the invention has many applications, it has particular utility in connection with computerized tomographic (CT) scanners. Accordingly, it will be described here in that context.

BACKGROUND OF THE INVENTION

The computerized tomographic (CT) scanner is a fairly recent development which facilitates examining a body by means of high energy radiation such as X- or gamma-radiation. Using such apparatus one can produce radiographs in any convenient form such as a picture on a cathode ray tube or other image forming device or a photograph of such a picture.

Scanners of this type direct radiation from an external source through the part of the body of interest. The radiation is in the form of a set of beams which are directed from a plurality of different directions toward one or more radiation detectors disposed on the opposite side of the body part from the radiation source. Each beam is detected after it has passed through the body and the outputs of the detectors are processed and correlated by a computer in such a way as to determine the absorption or transmission co-efficients of the elements in a two dimensional matrix of elements disposed in a plane of the body. This processed information is then used to produce a picture of that plane or slice through the body.

In the original type CT scanner made by EMI Limited, the body to be examined is inserted in an aperture in a scanning and locating structure which structure supports a radiation source and detector means therefor on opposite sides of the aperture. The source and detector means are movable back and forth on the structure so as to scan the radiation laterally across the body in a plane and the structure is also rotatable around the body about an axis perpendicular to that plane. A scanner such as that is shown, for example, in U.S. Pat. No. 3,919,552.

The main problem with that prior scanner is that the radiation source and detector arrays and the supporting structure therefor are relatively massive and their movement relative to the body as described above requires motive means and other ancillary equipment which makes the overall apparatus relatively complex, massive and expensive. Also because the body is scanned mechanically, the scanning operation is slow. Resultantly, a relatively long time, i.e. many seconds, is required to complete a scan in order to develop a useful image of a body slice. Consequently, movements of the patient's organs or body during the scan time introduce artifacts into the resultant picture which may obscure parts of the picture and confuse the radiologist. More importantly, however, because they are so slow, such prior scanners are incapable of achieving a rapid sequence of images of dynamic organs such as the beating heart.

More recently, there has been developed a CT scanner having a fixed circular detector array which encircles the patient's body and a radiation source which rotates about the body illuminating a selected plane or slice thereof with a radiation fan beam. The unabsorbed radiation is detected by a different set of detectors for each source position and the information from all of the detectors is correlated to produce an image of that body slice.

While this prior scanner is advantaged in having a fixed detector array, it still requires the mechanical structure to rotate the source in order to produce usable information. Accordingly, it also has a relatively slow scan time, e.g., several seconds for an accuracy of $\pm 0.5\%$ or better which is too slow to produce snap shot images of dynamic organs such as the heart. Moreover, it is still relatively complex and expensive because it requires the mechanical structure and motive means necessary to rotate the source. A scanner of that type is made by American Science and Engineering Inc. and is disclosed in that company's publication ASE-3869, dated April 1976 entitled Computerized Tomographic Scanner.

It has also been proposed to construct a scanner in which both the source and the detector array are fixed to avoid some of the aforesaid problems. Two different species have been proposed. In the first, presently under construction at the Mayo Clinic, Rochester, Minn., the source array consists of a fixed array of separate X-ray tubes situated on a semicircle around the patient's body. These tubes are pulsed in sequence to develop a rotating radiation beam which illuminates multiple slices of the patient's body. The emergent radiation is then detected by a fixed semicircular array of detectors diametrically opposed to the radiation source. The signals from the detectors are then processed to develop the picture of the body slice.

While this arrangement has no moving source and detector structure, it is extremely expensive because in order to obtain a reasonably good picture, as many as 28 separate X-ray tubes complete with supporting circuitry and shielding are required. Further, these tubes are relatively bulky so that the different source positions are necessarily spaced relatively far apart. Consequently, the resultant picture does not contain as much information as it should. To compensate for the small number of source positions, the device may have to be rotated slightly during the scan. This requirement, which partially negates the advantages afforded by a stationary scanner, will add to the mechanical complexity and also increase the scan time of the device.

The other proposed species of stationary scanner described in The Journal of Computer Assisted Tomography, Vol. 1, No. 4 dated October 1977 employs a fixed radiation source in the form of an electron beam gun oriented along the patient axis. A ring of X-ray emitting material encircles the patient as does an adjacent fixed circular detector array. The beam from the electron gun is deflected in a circle so that it scans around the target ring causing that ring to emit X-rays radially inward toward the patient. The radiation emerging from the opposite side of the patient is detected by the detector array and the detector signals are processed to develop the picture of the selected slice through the patient's body.

While this type of scanner may have a potential scan time which is fast enough to depict the beating heart in real time, it would be extremely large and bulky because the long (e.g., 3 meters) path of the electron beam from the gun to the target ring must be completely enclosed within a high vacuum chamber (about $10^{-7}$ Torr) to prevent undue electron beam dispersion. Also, a very high current electron beam is required for a fast scan time. Owing to repulsive space charge effects, the beam would be quite difficult to control with the requisite precision (small focal spot size, beam position, etc.) needed to produce a useful picture. For these same reasons, that type of CT scanner would be quite expensive to make and maintain.

None of the presently available CT scanners scan and process information fast enough to produce real time pictures of the beating heart. Rather, they will have to resort to cardiac gating techniques involving averaging the data collected for a given cross-sectional slice of the heart over a series of heart beats. Gating techniques are inherently inaccurate owing to the spatial and temporal non-reproducibility of the heart from beat to beat, and the pictures produced thereby may be degraded by motion artifact blurring.

SUMMARY OF THE INVENTION

Accordingly, it is an object of the present invention to provide improved radiation imaging apparatus having fixed X-ray source and detector arrays.

Still another object of the invention is to provide such apparatus in a CT scanner which, with fixed source and detector arrays, should achieve millisecond scan times to acquire a given picture.

Still another object of the invention is to provide a scanner which produces images characterized by low noise with high spatial and temporal resolution.

Another object is to provide such a scanner which during a given heart beat, should acquire a sufficiently low noise, high spatial resolution static image of the beating heart in its relaxed state to distinguish ischemic heart tissue from normal tissue and to detect, size and localize myocardial ischemia and infarctions.

A further object is to provide an ultra-fast CT scanner which should rapidly acquire X-ray data for a sequence of images of the beating heart.

A further object of the invention is to provide a cardiac CT scanner which should accomplish both static and dynamic tasks without resorting to cardiac gating techniques.

A further object of the invention is to provide a CT scanner which is relatively compact.

A further object of the invention is to provide such radiation imaging apparatus which has a relatively low input power requirement.

Still another object is to provide an improved pulsed X-ray source capable of producing a relatively constant optimized radiation output for an appreciable time interval.

Another object is to provide a compact X-ray source having a relatively long operating life.

A further object is to provide such a source which facilitates obtaining relatively high contrast radiation images of the body.

Yet another object of the invention is to provide an improved pulse power supply for such a source.

Other objects will, in part, be obvious and will, in part, appear hereinafter.

The invention accordingly comprises the features of construction, combination of elements and arrangement of parts which will be exemplified in the following detailed description and the scope of the invention will be indicated in the claims.

In general, the present apparatus employs a fixed array of discrete radiation sources and an adjacent fixed co-axial array of closely packed radiation detectors. The diameters of the arrays are such that a patient can be adjustably positioned along their common axis so that a radiation image may be obtained of a selected slice through the patient's body. The radiation sources are pulsed by a separate, relatively inexpensive, compact high voltage pulse generator, with each source position producing a radiation fan beam which is directed toward the pre-selected part of the patient's body. The unabsorbed radiation emerging from the opposite side of the patient's body is detected by detectors in the detector array and the electrical outputs from those detectors are digitized and read into a computer.

As each successive radiation source in the array is pulsed, corresponding detector information is obtained and stored. At the end of a complete scan, when all of the sources have been interrogated, the collected information is correlated and processed by the computer to produce a reconstruction image of that selected slice through the patient's body. The data from the computer is then used to display the image on a cathode ray tube.

Each radiation source in the source array comprises a special, small, inexpensive, compact cold cathode diode assembly. It should be mentioned at this point that cold cathode diodes have been used heretofore as X-ray sources. However, the prior uses have been confined primarily to nuclear weapons effects simulation applications in which very low impedance diodes (e.g., a few ohms) are driven by very short (about 50 ns), very high-voltage pulses (about 1 megavolt) to cause the diodes to produce very short, highly intense X-ray bursts which would be totally unsuitable for radiation imaging applications and indeed would seriously injure, if not kill, a patient.

Applicants are also aware of a field emission X-ray tube in the nature of a cold cathode diode manufactured by Field Emissions Corp., now a division of Hewlett-Packard, having a relatively high impedance on the order of 300 ohms which is used in medical radiology somewhat like a standard X-ray tube. The diode has a truncated conical tungsten anode and four comb-shaped cathode arrays distributed around the anode. The diode is driven in a multiple pulse mode by short, i.e., 30 ns, high voltage pulses whose amplitude is on the order of 350 Kv.

However, that type tube has several drawbacks which militate against its use in imaging apparatus of the type with which we are concerned here. The tube is quite complicated to make and it is about six inches long and also requires a high, e.g., $10^{-7}$ Torr, vacuum so that such tubes cannot be packed sufficiently closely in a scanner array, at least not without employing a bulky vacuum manifold and ancillary very expensive high vacuum equipment. Also, the high voltage pulses which drive that tube cause the tube to generate relatively hard X-rays which are unsuitable in the present application because they produce poor contrast images of tissues.

Furthermore, with its high voltage, short pulse operation, there is insufficient time to dissipate the heat produced in the tube anode due to impinging electrons. Therefore, the tube has a relatively short life. Such high voltage operation also requires that tube to have a very complicated insulator structure separating the anode and the cathode arrays to minimize electrical conduction across the insulator surface which tends to materially reduce the tube impedance and hence reduce its X-ray output. That problem is exacerbated by the fact that such surface conduction is promoted or enhanced by the ultraviolet radiation which invariably accompanies the production of X-rays.

The short (30 ns) duration pulsing of that tube also demands a relatively complicated pulse power supply because the supply must generate pulses having a very fast rise time. This, in turn, requires that the overall circuit have a relatively low inductance since the rise time is directly proportional to inductance. This requirement for low inductance makes the packaging of many such tubes in an array and the distribution of such pulses to the various tubes extremely difficult and expensive.

Finally the operation of any field emission device produces a so-called cathode plasma which propagates from the cathode toward the anode thereby reducing the tube impedance and lowering its X-ray output. The speed of that plasma varies directly as the rise time of the voltage pulses driving the tube. Consequently only a very brief burst of X-rays can be emitted from the tube. These and other considerations militate against the use of that pulsed X-ray source in radiation imaging applications of the type with which we are concerned here.

We have found, however, that when a cold cathode diode having a high impedance of greater than 100 ohms and most preferably 300 to 350 ohms is driven by relatively low voltage pulses on the order of 120–125 KV which are of long duration e.g. 150 to 160 ns, the diode functions as a superior X-ray source in radiation imaging applications, and particularly in an ultrafast tomographic scanner for producing high contrast images of the body. The pulsing of the diode at such low voltage causes it to generate sufficiently soft X-rays as will obtain good image contrast.

One would think that such a reduction in the operating voltage of the diode would worsen already potentially serious problem of diode anode damage due to excessive heat. This is because lower energy electrons emitted by the diode cathode are known to penetrate less deeply into the anode so that the heat generated thereby is absorbed by a thinner anode layer and takes longer to dissipate. Unexpectedly, however, this is not the case. Apparently the concomitant use of a long duration pulse seems to allow sufficient time for the heat to diffuse into the deeper and cooler anode layers, particularly in the case of the applicants' novel diode constructions to be described later.

The utilization of low voltage, long duration pulses which inherently have a relatively long rise time to drive a high impedance diode source also considerably relaxes the requirements of the pulse generator in that a higher circuit inductance can be tolerated. This makes it much easier to pack the sources in an array and to distribute the driving pulses to the different sources at the rate required for a tomographic scanner, e.g. 10 kHz.

It should be mentioned at this point that is is not immediately obvious to drive a high impedance diode with a long duration pulse if the objective is to produce an X-ray source having a uniform radiation output. This is because it is known that field effect devices such as cold cathode diodes suffer impedance collapse due to various phenomena during the time that they are pulsed. One such phenomenon is the expanding cathode plasma described previously whose speed varies with the rise time of the voltage pulse. Thus even though the longer driving pulse has a slower rise time, still the diode impedance, and therefore its voltage, will drop during the long pulses as the cathode plasma propagates at a rate of about 1.7 cm/per Msec. toward the anode and the X-ray output from the diode will drop commensurately. Actually, for a 300 ohm diode requiring an anode-cathode gap of about 7 mm, the impedance falls by a factor of two during a 150 ns pulse.

In addition, however, there is an anode plasma created from gasses desorbed from the anode which forms when the anode is heated to a temperature of only about 400° C. This can occur quite quickly (e.g., 2 to 10 ns). This plasma produces low Z ions which quickly transit the anode-cathode gap. These ions partially charge neutralize the electron space charge in the diode and cause an abrupt drop in diode impedance. This, in turn, lowers the diode voltage and its X-ray production. The anode plasma itself also propagates toward the cathode and contributes to faster impedance collapse and thus a drop in the X-ray output from the diode. Because of these gap closure problems one would tend to dismiss the idea that a cold cathode diode could be an effective X-ray source in imaging apparatus such as a CT scanner which requires a relatively constant reproducable output.

We have found that the diode impedance collapsing anode plasma can be substantially reduced by preheating the anode to 200° to 400° C. to drive off the desorbed gasses temporarily from the anode surface by prepulsing the diode one or more times just prior to pulsing it for data acquisition purposes. Also since the impedance of the diode is relatively low giving rise to higher current through the diode during prepulsing as the plasma forming gasses are driven off, a shorter diode driving pulse may be employed to prevent overheating or melting of the anodes. Once the diode surface is purged of those relatively low temperature desorbed gasses, no additional anode plasma is produced until the anode is heated to its melting temperature, about 3650° C. for a tungsten anode. We believe at that point the phase transition of the anode material from solid to liquid releases additional desorbed material formerly trapped in the tungsten lattice.

The effects of anode plasma on diode output can be reduced even more by proper construction of the diode as will be described in detail later.

Further, we have discovered that the diode impedance-reducing cathode plasma phenomenon can be compensated for by intentionally mismatching the impedance of the diode and the output impedance of its pulse generator. We knew from work done by others that for a pulse generator of given output impedance $Z_G$ with its pulse forming line charged to a fixed voltage $V_G$ that the maximum diode radiation pulse in the spectral region of interest in tomography defined as $I_D V_D^{2.8}$, ($I_D$ and $V_D$ being the voltage and current affecting the diode), would occur when the diode impedance $Z_D = V_D/I_D = 2.8 Z_G$. Therefore it occurred to us that if the diode impedance $Z_D$ is allowed to drop due to the cathode plasma from a value greater than 2.8 $Z_G$ to a value less than 2.8 $Z_G$, the diode voltage $V_D$ would also drop, but its current $I_D$ would rise yielding an optimized substantially constant radiation pulse $I_D V_D^{2.8}$. In fact, for best results in the application of interest here, the diode impedance $Z_D$ should be about 4 to 5 times the generator impedance $Z_G$.

In sum then we have chosen the diode source impedance, and the voltage and duration of the pulses driving the diode so as to minimize anode damage upon the occurrence of each pulse in order to increase diode lifetime and long term reproducibility. The utilization of the long duration, low voltage pulses to drive the high impedance diode source configurations to be described in more detail later also considerably relaxes the requirements of the voltage pulse generator used to drive the diodes as X-ray sources. This, in turn, permits utilization of a relatively simple, low cost pulse power supply to drive the X-ray sources in the present scanner.

Furthermore, to offset the relatively poor reproducibilty of such pulsed diodes, the reconstruction algorithm used in the present scanner treats the acquired data as X-ray source fans, rather than detector fans so that each discrete X-ray source constitutes a view and each of the detectors in the array which is illuminated by the fan beam constitutes a ray. With this arrangement, it can be shown that only approximately 150 sources or views produce satisfactory reconstruction images with the introduction of only relatively small amplitude artifacts. Furthermore, the images are insensitive to changes in diode reproducibility on the order of several percent and which can be as high as 10%, in comparison with the very low, e.g. 0.1%, X-ray source reproducibility required in the prior scanners described above.

Each cold cathode X-ray source in the present apparatus comprises a self-contained unit or assembly having its own plugable cable to the power supply and its own inverse compensating X-ray filter and collimator. Further, the assembly is easily removable and replaceable at its appointed location in the source array so that it can be serviced or replaced with a minimum of effort. In a given scanner, the diodes to be described later are arranged to provide either a point or a line source of X-rays and a typical source array employs on the order of 150 discrete sources. However, in applications requiring higher spatial resolution images of organs such as the brain, the source array can be indexed through very small angles to build up 300 or even 600 views as will also be described in detail later. The source array housing in which the source units are located does have to be evacuated. However, only a modest vacuum is required, on the order of 0.5 microns, which is quite easy to maintain using a simple conventional vacuum pump.

As alluded to previously, the utilization of low voltage, long duration pulse driven high impedance diode sources in the present scanner greatly simplifies the pulse power source required to drive the diode sources. Actually, the present system utilizes a standard, unregulated, relatively low power supply of only 15 to 30 KV D.C. That supply feeds a primary capacitor which stores the energy for an entire scan comprising 150 pulses for a 150 diode source array. For reasons of cost and simplicity, the system uses a stacked coaxial cable transformer which provides both pulsed energy storage and also serves as a pulse forming network. The utilization of this inherently high impedance pulse forming network is made possible by the choice of even higher impedance diodes. The voltage step up ratio and the output-to-input impedance ratio are functions of the number of stages of gain in the cable transformer. By balancing the trade-offs between these parameters, the transformer is designed to have an output impedance appropriate for the diode sources and is arranged to deliver a 120 KV rectangular pulse when charged to, say, 20 KV by the charging capacitor. The pulse duration is directly related to the cable length, which can be altered if necessary. Also the high mass of cables provides heat dissipation between multiple pulses to a given source.

Upon application of a trigger signal, the input end of the transformer is shorted to ground via a switch. When the voltage across the transformer reaches the desired value, e.g., 20 KV, the switch short-circuits the transformer input causing the transformer to deliver a driving pulse to a diode source. In actual practice, the switch opens and closes at a rate of about 10 kHz so that the transformer produces a train of high voltage pulses which are applied by way of a rotary switch or distributor to the diodes in the source array, preferably non-sequentially, during each complete scan of the scanner.

Thus even though the pulse power source uses an unregulated power supply, the source produces high voltage pulses which are themselves regulated in the sense that the switch does not close unless the voltage across the transformer is the correct magnitude. Moreover the transformer itself, comprising a pulse-forming network, shapes each output pulse so that the pulse reproducibility is quite high.

As described previously, the high diode impedance and longer pulse width also allow high circuit inductance which, in turn, permits the use of a relatively simple high voltage distributor similar to an automobile distributor to switch between sources rather than a large number of complicated triggered high voltage switches, one for each diode. Those high voltage switches can now be replaced by a single conventional low voltage hydrogen thyratron operated in a rep rated mode.

The detector array in the present scanner comprises a multiplicity of X-ray detectors arranged in a ring spaced parallel from the diode source array. In order to obtain adequate information to produce relatively high resolution reconstruction images, a relatively large number, e.g. 750 detectors, are distributed in the array. In one scanner embodiment, conventional scintillation crystals are packed together around a ring, each being connected by a separate light pipe to a standard photomultiplier tube. X-rays incident on the crystal cause the crystal to scintillate, its light emissions being coupled to the photomultiplier tube which thereupon produces an output signal proportional to the intensity of the X-rays incident on the crystal. During a given scan, the signals from the detectors are digitized and processed to produce the reconstruction image. Alternatively, even more closely packed detector arrays can be obtained using conventional low-gain photodiodes which are reasonably stable. Gaseous or liquid ionization chambers can likewise be employed as X-ray detectors.

The present scanner employing fixed arrays of source diodes and detectors is able to attain high resolution reconstruction images of the human body with a scan time as low as 15 msec. Consequently, the scanner is able to produce reconstructed images of high quality of dynamic organs such as the beating heart. Moreover it can acquire high spatial resolution (e.g., 2 mm), low noise (e.g., about 1%) static images of the heart to assist in the diagnosis of heart ailments and to monitor the course of treatment. Therefore, the scanner should find wide application in hospitals, diagnostic clinics and the like.

BRIEF DESCRIPTION OF DRAWINGS

For a fuller understanding of the nature and objects of the invention, reference should be had to the following detailed description, taken in connection with the accompanying drawings in which:

FIG. 1 is a view partly diagrammatic with parts broken away and partly in block form showing a CT scanner embodying the principles of this invention;

FIG. 2 is a side elevation with parts broken away showing a portion of the FIG. 1 scanner;

FIG. 3 is a sectional view along line 3—3 of FIG. 1 with parts cut away showing elements of the scanner in greater detail;

FIG. 4 is a sectional view along line 4—4 of FIG. 3;

FIG. 5 is a fragmentary sectional view of another X-ray source embodiment;

FIG. 6 is a block diagram showing the pulse generator portion of the FIG. 1 scanner in greater detail;

FIG. 9 is a graph explaining the operation of the FIG. 3 X-ray source;

FIG. 10 is a fragmentary perspective view of a modified X-ray source array, and

FIG. 11 is a diagrammatic view of still another source array.

DESCRIPTION OF THE PREFERRED EMBODIMENTS

Figure 7:
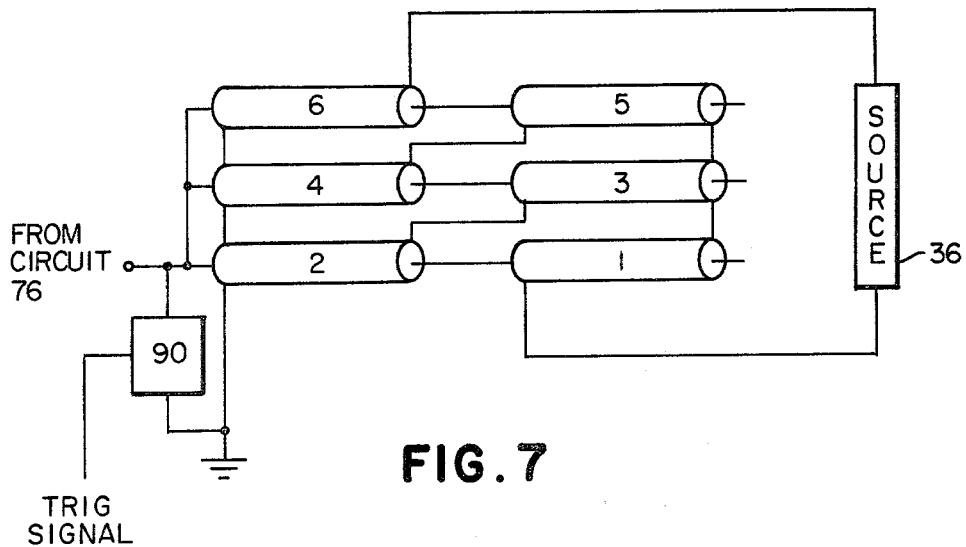
FIG. 7 is a diagrammatic view illustrating a part of the FIG. 6 generator in more detail.

Referring to FIG. 1 of the drawings, the present scanner illustrated generally at 10 is generally toroidal in shape and arranged to rest on the floor. The scanner has a large central opening 11 which is on the order of one meter in diameter to enable a patient positioned on a table T to be selectively positioned lengthwise in the scanner opening 11.

The scanner 10 includes a housing 12 containing an annular X-ray source section shown generally at 14 and an adjacent coaxial annular X-ray detector section indicated generally at 16. The source section 14 is serviced by a remote high voltage pulse generating section 22 and a vacuum pump 24 connected to section 14 by a hose 15. In response to pulses from generator 22, section 14 produces fan beams of X-rays which illuminate a selected cross-sectional slice of patient P. The detector section 16 detects the radiation which is not absorbed by the patient's body and delivers output signals via an output section 26 to a computer 28. The computer processes the signals from the detector section 16 and develops an image of that selected body slice, which image is displayed on a CRT monitor 32.

Turning now to FIGS. 1 to 3, the source section 14 comprises an annular tubular ring 34 which supports an array of discrete X-ray sources 36. The illustrated array is circular. However it could be arcuate or even linear in some applications. Hose 15 from pump 24 is connected to the interior of the ring in order to evacuate the ring. For ease of illustration, only a relatively few, widely spaced sources 36 are shown in the drawing figures. In actual practice, a typical source section 14 would contain on the order of 150 sources 36 closely packed around the periphery of the ring 34.

As best seen in FIGS. 2 and 3, each source 36 projects through an opening 38 in the outer wall 34a of ring 34 and is oriented so that it is directed radially inward toward the axis A—A of the scanner. Each X-ray source 36 comprises a compact self-contained cold cathode diode D, each source occupying about 2 cm of circumferential space. Each diode includes a generally cylindrical conductive shell 40. Positioned axially in the shell is a relatively large diameter, generally cylindrical metal conductor 41. Conductor 41 is supported more or less midway between the ends of shell 40 by an insulating plastic feedthrough 42 which also serves to electrically insulate the shell and conductor. Desirably an O-ring seal 43 is seated in a circumferential groove 44 formed in the conductor adjacent the feedthrough. A similar, larger diameter seal 45 is seated in a groove 46 formed in the inside wall of shell 40 opposite the feedthrough. The purpose of the seals is to isolate the opposite ends of shell 40 since a vacuum is maintained in ring 34 as described above. The vacuum insulating feedthrough region should be carefully designed so as maintain minimum diameter for maximum diode packing efficiency.

Mounted at the free end of conductor 41 is a relatively small diameter rod-like anode 48 which projects along the axis of shell 40 and extends more or less to the inner end of that shell. Typically anode 48 is on the order of 1 to 3 mm in diameter and 1 to 2 cm long. The annular segment of shell 40 adjacent anode 48 functions as the diode cathode 52 being of comparable length as the anode and having an inner diameter of 1 to 2 cm. One or more field enhancement rings 53 may be distributed along the inside wall of cathode 52 whose inner edges act as the source of the electron flow from the cathode to the anode where the generation of X-rays occurs. The role of these rings is to enhance the electric field on the inner surface of the cathode so as to promote early formation of the cathode plasma through cathode whisker explosion when the diode is pulsed. This cathode plasma then provides the source of the electrons which produce the X-rays.

Each diode D is provided with a high-voltage co-axial cable 58 which extends into the outer end of shell 40. The central conductor of the cable is connected to the outer end of conductor 41 adjacent the feedthrough, while the outer cable conductor is connected electrically to shell 40 preferably by way of a metal cover 59 which is secured to the adjacent end of the shell and through which cable 58 passes. The space inside shell 40 between feedthrough 42 and cover 59 is desirably filled with a suitable oil or potting compound 60. Each cable 58 is arranged to be connected to the high voltage pulse generator 22 (FIG. 1), with the outer conductor of the cable being maintained at or near electrical ground. To facilitate this, each cable 58 desirably terminates in a co-axial connector plug (not shown) which plugs into a mating connector in generator 22.

Shell 40 is provided with an integral flange 40a having a circumferential array of openings 61 arranged to receive a set of bolts 62 which are turned down into threaded openings 63 in the ring wall 34a to secure the source to the ring. Also an O-ring 64 is seated in a groove 65 formed in the underside of the flange to provide a fluid-tight seal between the flange and the ring wall. Thus each source 36 comprises a unitary self-contained diode-cable assembly which can be unplugged from generator 22 and detached from ring 34 quite easily for purposes of repair or replacement. When each source 36 is bolted in place as shown in FIG. 3, there is sufficient sealing engagement between the source and ring 34 so as to enable the pump 24 (FIG. 1) to maintain a moderate vacuum on the order of one micron inside ring 34 which is quite sufficient to enable all of the cold cathode diode sources 36 to operate properly.

Mounted radially inward from each diode anode 48 is an inverse compensating filter 66. Preferably, as shown in FIG. 3, the filter 66 is mounted in an opening 67 in the ring inner wall 34b. The purpose of the filter is to reduce the radiation at the outer portion of the X-ray fan beam produced by each source 36. This filter is a conventional gradient density filter made of a suitable X-ray absorbent material such as aluminum or copper.

In accordance with this invention, the anode 48 and cathode 52 of each source 36 comprise a cold cathode diode D having an unusually high electrical impedance $Z_o$, in excess of 100, and most preferably 300 to 350 ohms. When pulsed from a high voltage source, the electrons emitted from the cathode enhancement rings 53 bombard the anode 48 of the diode producing a burst of X-rays shown at X in FIG. 3. With the radially oriented X-ray source 36, the X-rays are emitted generally from the end of anode 48 so that the focal spot size of each source more or less equals the anode diameter, i.e. 1 to 3 mm. This focal spot size is more than adequate for cardiac images as well as being sufficiently small to produce high quality images of the body generally.

As is the case with X-ray sources generally, this production of X-rays is accompanied by the generation of ultraviolet radiation. This radiation may have a tendency to precipitate electron migration along surface 42a of the plastic feedthrough 42 nearest anode 48. Any such tendency would undesirably lower the impedance of the diode. Accordingly, to minimize that tendency, an integral flange 41a is formed at the free end of conductor 41 which functions to shield the feedthrough surface 42a from the ultraviolet radiation produced by the X-rays emitted from the end of anode 48.

In the source 36 illustrated in FIG. 3., the anode 48 and the cathode 52 are made primarily of carbon and graphite. Preferably POCO brand graphite should be used particularly for the enhancement rings 53 because it has a very fine grain enabling it to be formed into very thin (0.005 inch) sheets and be strong enough to withstand machining to the required dimensions thereby providing a diode which is relatively easy to make and is long lived. Preferably the anode should have a thin, high Z (tungsten) X-ray producing layer. The cathodes could also be made of a conductive metal. Carbon is suitable because it is quite heat resistant, is transparent to X-rays and generally makes a diode source having a fairly reproducible output. Most preferably, the anode 48 is a composite structure such as shown in FIG. 4, the various material thicknesses being exaggerated for clarity. It comprises a carbon core 68 which is surrounded by a coating 69 of tungsten or other metal having a relatively high atomic number. The tungsten coating is sufficiently thick to produce a high yield of X-rays, yet thin enough not to self-absorb these X-rays. It is also thin enough to dissipate heat to the carbon substrate during the pulse so as not to heat up to its melting temperature. Finally, the anode may include a very thin (e.g., a few microns) outer coating or jacket of carbon or other suitable material 70. This layer has two functions. The first is to mechanically contain the tungsten material. This minimizes the tendency of the tungsten to ablate from the anode and coat the cathode structure, particularly at the edges of the field enhancement rings 53 which effect might mask the desirable carbon characteristics or properties of the cathode. Its second, and possibly more important function is to give the anode a higher threshold than tungsten for production of the anode plasma from desorbed gases released by electron bombardment to maintain reasonably high diode impedance all during the pulse.

Also in some applications, it may be desirable to taper anode 48 to minimize self-absorption of X-rays along the surface of the anode. A source such as this is indicated generally at 36a in FIG. 5. In that source, the anode 48a is tapered along its length, typically at an angle of about 12°.

Referring now to FIG. 6, the high voltage pulse generator 22 which pulses sources 36 comprises a DC power supply 72. However, in sharp contrast to the large, expensive high voltage (e.g., 120 KV.) regulated supplies required with conventional X-ray tubes in CT scanners, the power supply 72 is unregulated and has a relatively low output voltage in the order of 15–30 KV. Consequently, its cost can be as much as five times less than the regulated supplies heretofore used in CT scanners.

Supply 72 feeds a primary capacitor 74 connected between its output and ground. This capacitor (e.g. 50 Mfd.) is used to store the energy for each scan of the scanner, i.e. 150 pulses. The voltage across the capacitor is applied to a charging circuit 76 comprising simply a resistance 79, an inductance 80 and a diode 82. The output of circuit 76 is fed to a pulse forming network 84. The primary capacitor 74, the charging circuit 76 and network 84 together form a resonant charging system so that, assuming infinite Q (resistance 79 equal to zero) the peak voltage delivered to network 84 is theoretically twice the output voltage at primary capacitor 74. The pulse forming network 84 to be described presently performs not only a pulse forming function, it also provides pulse energy storage and serves as a step-up transformer.

When circuit 76 charges network 84 to the required voltage, a trigger signal is issued to a hydrogen thyratron switch 90. Thereupon network 84 discharges, applying a properly shaped high voltage pulse to cable 86 which is connected to a high voltage distributor 92. The latter device selectively routes the high voltage pulse to one of the cold cathode diode sources D1 to D150 via its corresponding high voltage cable C1 to C150. Application of the high voltage pulse to one of the cold cathode diodes D1 to D150 in X-ray generating section 14 (FIG. 1) causes the selected diode to emit a burst of X-rays.

Turning now to FIG. 7, pulse forming network 84 comprises preferably a stack of coaxial cables connected to form a coaxial line generator or transformer. That figure illustrates a network 84 having six such cables numbered 1 to 6. In actuality, a typical scanner might employ ten cables, each having an impedance of 10 ohms so that the total output impedance of the network is 100 ohms.

As seen from FIG. 7, the network cables are connected in pairs. For example, cables 1 and 2 form one pair. Cables 3 and 4 form a second pair, and so on. The output from circuit 76 is applied in parallel to the central conductor of one cable of each pair (i.e., cables 2, 4, 6) which constitutes the input of the pulse forming network as a whole. The opposite end of that central conductor is connected to the central conductor of the second cable in each pair (i.e., cables 1, 3, 5), the opposite end of the latter of which floats. The left ends of the outer conductors of cables 2, 4 and 6 in the stack are connected to each other and to ground. The right ends of those conductors in cables 2 and 4 are connected to the left ends of the outer conductors of cables 3 and 5 respectively. Also, the right end of the outer conductor of cable 6 and the left end of the outer conductor of cable 1 are connected to the load, which in this case is a diode source 36. Finally, the thyratron switch 90 which is triggered by a TRIG signal is connected between the network input and ground, that signal being provided by any conventional controllable pulse generator at each position of distributor 92.

With switch 90 open, when a voltage V from circuit 76 is applied to the network input, each cable charges up in parallel so that a voltage V appears across that cable. However, the voltage vectors in each pair of cables oppose one another so that the net voltage applied to the source 36 is 0 volts. However, when the input to the one cable of each pair is short circuited by closing thyratron switch 90, there is a vector reversal of the voltage propagating through those cables so that all of the cables discharge in series whereby a voltage pulse is applied via distributor 92 to a diode source 36. The magnitude of the voltage pulse into an open circuit equals the input voltage V times the number of cables, i.e. six in FIG. 7. The characteristic generator impedance equals Zo times the number of cables, where Zo is the characteristic impedance of one cable.

Thus in each position of distributor 92, with switch 90 open, the charging circuit 76 commences charging each of the cables 1 to 6. When the voltage across the cable stack reaches the selected value, e.g., 20 KV, after a fixed time interval a TRIG signal is issued to switch 90 which short circuits the cable inputs so that the transformer delivers a high voltage pulse via distributor 92 to a source 36. This pulse which is rectangular with a duration on the order of 160 ns turns on diode source 36 so that it produces a burst of X-rays X (FIG. 3).

Figure 8:
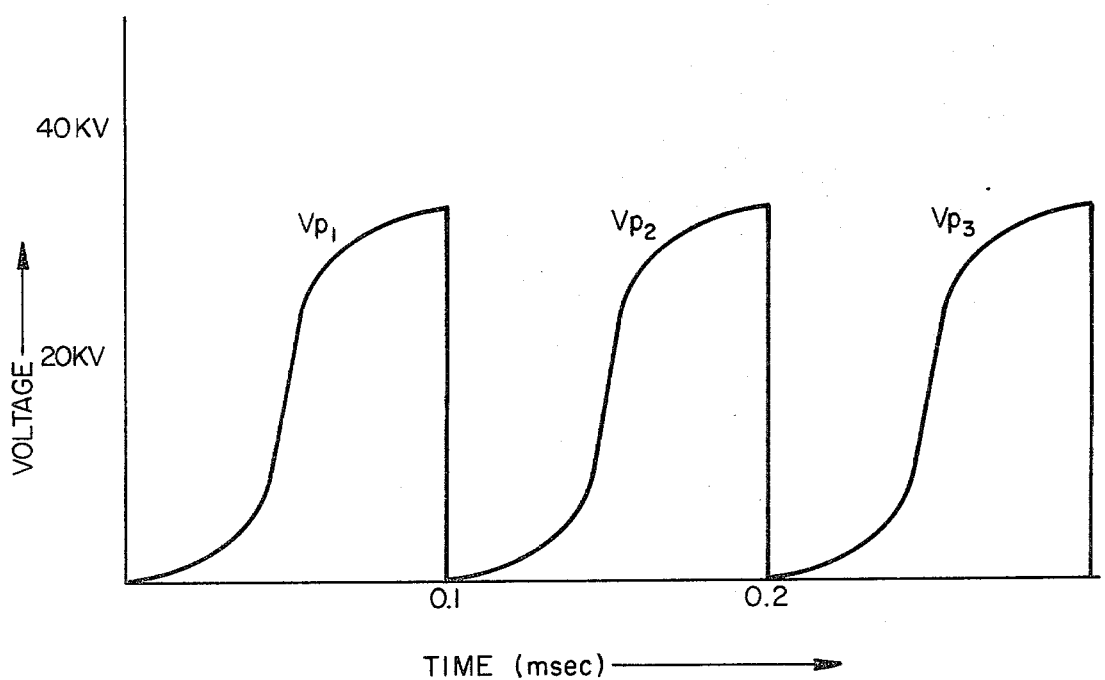
FIG. 8 is a graph explaining the operation of the FIG. 6 charging circuit.

The operation of the FIG. 6 pulse generator is illustrated diagrammatically in FIG. 8. At the beginning of each scan at time 0, a switch (not shown) in supply 72 is closed so that the supply charges the capacitor 74 whose operating voltage is, say, 20 KV. Consequently, the charging network 76 applies up to twice that voltage or 40 KV. to the pulse forming network 84. Network 84 commences charging, the voltage across the network being illustrated by waveform Vpl in FIG. 8.

When the voltage across the network 84 reaches the required value after a fixed period of time, a TRIG pulse is issued to switch 90 which discharges the stacked cables 1 to 6 (FIG. 7) so that a voltage pulse of 120 KV. is applied by way of distributor 92 to the first diode D1 in the source array. After the network 84 has been discharged, switch 90 opens and the distributor 92 is indexed conventionally to the next diode D2. Network 84 commences charging again as shown by the waveform Vp2 in FIG. 8. After the same time interval, switch 90 again fires, discharging network 84 so that a 120 KV. pulse is applied to diode D2 in the array. This process continues with the voltage pulses being applied at a rate of about 10 kHz until all 150 diodes in the source array have been pulsed, which requires about 2250 joules of energy, thereby completing the scan. Whereupon, capacitor 74 is recharged from the power supply 72 in preparation for the next scan. Alternatively, if capacitor 74 is sufficiently large, several complete scans can be executed before it has to be recharged.

Preferably diodes $D_1$ to $D_{150}$ are not in sequence in the source array. Rather, each successive diode that is pulsed is positioned in the array so that its fan beam does not overlap the beam produced by the previously pulsed diode. This extends the period available for the read out of the series of detectors in the detector array 16 which are illuminated by each pulsed diode D. Also to minimize the problem of diode impedance collapse due to anode plasma created by desorbed gasses discussed above, each diode is prepulsed prior to each 160 ns scan pulse with one or more lower voltage short duration pulses to heat the diode anode and drive off the gasses. This can be accomplished by incorporating a triggered crowbar switch (not shown) into the pulse generator to chop a long duration pulse from network 84 into one or more short lower voltage pulses.

To avoid patient exposure to X-rays during prepulsing, a small lead shutter (not shown) can be indexed into position in front of the filter 66 of the prepulsed diode.

FIG. 9 is a graph showing the voltage $V_D$ and current $I_D$ waveforms and the X-ray profile $I_D V_D^{2.8}$ which characterize a typical diode source 36. The waveform $R_c$ represents the effective diode cathode radius which changes due to the cathode plasma which propagates toward the anode during the long duration scan pulse. As seen from FIG. 9, there is no abrupt impedance $Z_D$ collapse due to the formation at low temperatures of anode plasmas after turn on because of the cladded diode anode structures and prepulsing described previously. Rather there is only a gradual decrease in diode impedance with time due to the gradually shrinking effective cathode radius $R_c$. By selecting a high impedance diode which starts out at an impedance $Z_D$ of in excess of 2.8 times the generator impedance $Z_G$ (80 ohms in this example) and preferably 4 to 5 times that value, 300 ohms in the example, and allowing the impedance $Z_D$ to drop through 2.8 $Z_G$ to 2 $Z_G$ or 160 ohms, the changes in diode voltage and current can be made to more or less offset one another. That is, the voltage $V_D$ falls from 126 KV at 40 ns to 108 KV at 160 ns, but the current $I_D$ increases from 420 A to 660 A during that time. Resultantly the diode radiation output $I_D V_D^{2.8}$ remains substantially constant all during the pulse once the diode turns on. By the time the matched impedance value of 80 ohms is reached at 260 ns, the radiation production efficiency of the diode has dropped to about 65% of its peak value. Thus if the diode is turned off after 160 ns most of the useful X-rays will have been extracted and the current $I_d$ will not have increased to the point where the diode anode becomes overheated to the point of its being damaged or producing the high temperature anode plasma due to anode melting. In other words, this technique keeps both voltage and radiation output about constant which produces the most X-rays for the least amount of anode heating.

Referring again to FIGS. 1 and 3, during each scan, each of the 150 diodes sources 36 is pulsed in turn thereby exposing the patient to successive bursts of X-rays originating at spaced locations around a circle, each burst having a fan angle of about 45° defined by collimators (not shown) in ring 39. The unabsorbed radiation from each diode source 36 is detected in the detector section 16.

Section 16 includes a tubular ring 98 spaced parallel from source ring 34. Secured to the inner edge of ring 98 is an array of radiation detectors indicated generally at 100. For the illustrated circular source array, a typical detector array has in the order of 750 detectors 100 closely packed around the ring 98 with their windows positioned close to or overlapping the source section 14 as shown in FIG. 3.

The detectors 100 may be of any standard type. The one shown in FIG. 3 comprises a scintillation crystal 102 which emits light when X-rays X are incident upon it. The light photons are coupled by a light pipe 104 to a conventional photomultiplier tube 106. Tube 106 thereupon emits a signal by way of an electrical lead 108 to output section 26 (FIG. 1) whose amplitude is proportional to the intensity of the incident radiation X. Thus at the beginning of a scan, when the first source 36 in the source array is pulsed, all of the detectors 100 in the 45° sector of section 16 directly opposite that source detect the unabsorbed radiation X and produce output signals coupled by leads 108 to output section 26. Section 26 digitizes the signals and loads the data into computer section 28.

When the second source 36 is pulsed, another 45° set of detectors produce output signals which are processed and applied to computer section 28. This process continues for all of the sources 36 so that at the end of a complete scan having a duration of about 15 msec, the computer 28 contains data sets from 150 source positions or views, each set consisting of about 175 rays from a 45° sector of detectors 100. Section 28 processes and correlates all this data to develop a reconstruction image of the selected slice or plane through the patient P.

Because of its fast scan time, the present system is able to obtain reconstruction images of dynamic organs such as the beating heart. However, some reconstruction images might require more than 150 different source positions during each scan because of reduced X-ray transmission through certain regions of the body such as the brain and abdomen or the need for increased spatial resolution. In this event, additional views may be obtained with the present apparatus to build up 300 or even 600 positions during a given scan simply by indexing the source section 14 through a small angle relative to the detector section 16. A suitable mechanism for accomplishing this is indicated in FIG. 2.

As seen in that figure, the source ring 34 is suspended within housing 12 by four radially oriented flexures 150. Mounted on the outside wall 34a of ring 34 is a rack 152 that meshes with a rotary pinion 154 driven by small stepping motor 156 secured to the inside of housing 12. After the system acquires data from the 150 sources 36 as described above, the motor 156 can be activated to rotate the source array through a small angle to displace the sources 36 a few millimeters at which point data from a new set of positions may be acquired. Also in this case due to the reduced X-ray transmission through those regions of the body, each diode source 36 may be multiple-pulsed at each given source position to optimize the reconstruction image.

The diode sources 36 specifically illustrated in FIG. 2, being radially oriented, constitute point sources of X-rays. It should be understood that those sources could be oriented axially, i.e parallel to axis A, and so function as line sources in those applications where a line source array is preferred.

Also, instead of using individual X-ray source assemblies 36, it is also possible to form a source array as a single unit. FIG. 10 illustrates an arrangement of this type wherein the source array comprises a set of radially oriented anode rods 160 distributed around in a circle whose center is the scanner axis A. Spaced above and below the anode rods are a pair of continuous ring-shaped plates 162 and 164. The anode rods 160 may be cladded tungsten rods as described above or tungsten wires. The plates 162 and 164 are desirably made of carbon. Joined to these plates are thin field enhancing carbon sheets or blades 163 and 165. These sheets may be perpendicular to the rods as shown or parallel to them. The diode array 158 can be housed in a suitable toroidal housing (not shown) and connections made to the cathode plates and individual anode rods from the pulse generator in much the same manner discussed above in connection with the source assemblies 36.

FIG. 11 shows still another source array indicated generally at 166. In this arrangement a series of plates are distributed around a circle whose axis is a scanner axis A. Every other plate is connected to ground. The interstitial plate e.g. plates 168a and 168b are connected by way of a distributor 92 (FIG. 6) to the pulse generator. The interstitial plate and its adjacent ground plates comprise a source diode. In this arrangement, since each plate has an edge parallel to the inner inner axis A, each diode constitutes a line source of X-rays. The plates may be made of carbon or cladded tungsten such as described above. This array has the advantage of permitting the diodes to be packed closely together to obtain maximum spatial resolution and to provide a maximum number of views in a given volume of space.

It will be appreciated from the foregoing, then, that the utilization of compact cold cathode diode assemblies as discrete sources in radiation imaging apparatus enables a large number of such sources to be arrayed closely together. Consequently when incorporated into a CT scanner, the array can remain fixed during a complete scan obviating the need for the complicated mechanical indexing mechanisms found in prior comparable scanners. Furthermore, the use of high impedance diodes as the X-ray sources and low voltage, long duration diode pulses enables the apparatus to use a pulse generator with only moderately low circuit inductance which generator derives its power from a relatively low voltage unregulated power supply resulting in a further cost saving. Moreover the pulse generator and diode assemblies together permit the source array to generate a large number of source fans in a very short time so that data representing a very large number of views can be acquired in a very short time enabling the apparatus to produce real time reconstruction images of dynamic organs in the body such as the beating heart.

It will also be seen from the foregoing that the objects set forth above among those made apparent from the preceding description are efficiently attained and that certain changes may be made in the above description without departing from the scope of the invention. For example, the same principles may be used in non-CT radiation imaging applications such as spatial multiplex tomography, coded source tomography and X-ray fluorescence excitation analysis. Therefore, it is intended that all matter contained in the above description or shown in the accompanying drawings shall be interpreted as illustrative and not in a limiting sense.

It is also to be understood that the following claims are intended to cover all of the generic and specific features of the invention herein described.

We claim:

1. In a computerized tomographic scanner:
    A. a fixed array of cold cathode diodes each said diode being characterized by an impedance in excess of about 100 ohms;
    B. a fixed array of radiation detectors juxtaposed to the diode array;

C. means for applying greater than 100 ns duration and less than 200 kv voltage pulses sequentially to the diodes in the array so as to cause said diodes to emit successive substantially constant amplitude X-ray pulses, said radiation being detected by the detectors in the detector array, and D. means responsive to the output signals from said detectors for producing a reconstruction image of a selected body slice illuminated by radiation from the diode array.

2. The scanner defined in claim 1 wherein the source and detector arrays are circular with a common axis and are positioned adjacent one another.

3. The scanner defined in claim 2 wherein each diode in the source array is arranged radially with respect to said axis so as to constitute a point source of X-rays.

4. The scanner defined in claim 2 wherein each diode in the source array is arranged parallel to said axis so as to constitute a line source of X-rays.

5. The scanner defined in claim 1 wherein each diode comprises:

A. a rod-like anode,

B. a generally cylindrical cathode arranged concentrically to the anode.

6. The scanner defined in claim 1 wherein the diodes comprise electrically conductive plates spaced adjacent one another, adjacent pairs of plates constituting a separate diode.

7. The diode defined in claim 6 and further including one or more electrically conductive field enhancement blades projecting from one plate toward the other in each plate pair.

8. The scanner defined in claim 5 and further including one or more electrically conductive annular field enhancement blades projecting from the cathode toward the anode.

9. The scanner defined in claim 5 wherein said cathode and anode are both comprised primarily of carbon.

10. The scanner defined in claim 9 and further including a thin coating of tungsten metal on said anode.

11. The scanner defined in claim 10 and further including a thin coating of carbon covering said tungsten coating.

12. The scanner defined in claim 5 wherein said diode anode comprises tungsten metal.

13. The scanner defined in claim 1 wherein the diodes in the array comprise

A. a pair of spaced-apart cathode plates, and

B. a set of anode wires spaced parallel to one another in a common plane between said plates.

14. The scanner defined in claim 13 and further including one or more field enhancement blades projecting from said cathode plate toward said wires, said cathode plates being oriented more or less perpendicular to said anode wires.

15. The scanner defined in claim 5 wherein a lengthwise end segment of said anode is inwardly tapered.

16. The scanner defined in claim 1 and further including means for pre-pulsing each diode prior to the application of said pulse to said diode with one or more no greater duration pulses to drive off desorbed gases from said diode anode.

17. The scanner defined in claim 1 wherein each said low voltage pulse is on the order of 120 to 130 KV. and has a duration on the order of 150 to 160 ns.

18. The scanner defined in claim 1 wherein each said diode has an initial impedance in excess of 2.8 times the output impedance of said pulse applying means.

19. The scanner defined in claim 18 wherein each said diode has an initial impedance that is 4 to 5 times the output impedance of the pulse applying means.

* * * * *